United States Patent [19]

Welch, Jr.

[11] 4,022,791
[45] May 10, 1977

[54] 2-AMINOMETHYL-3,4-DIHYDRONAPH-THALENES

[75] Inventor: Willard M. Welch, Jr., North Stonington, Conn.

[73] Assignee: Pfizer Inc., New York, N.Y.

[22] Filed: June 3, 1975

[21] Appl. No.: 583,420

[52] U.S. Cl. .................. 260/293.62; 260/247.2 A; 260/247.2 B; 260/247.7 Z; 260/268 BC; 260/306.7 E; 260/326.33; 260/326.5 M; 424/248.54; 424/250; 424/267; 424/270; 424/274; 424/248.58; 424/248.57

[51] Int. Cl.² ........................................ C07D 295/08

[58] Field of Search ............ 260/247.2 A, 247.2 B, 260/247.7 C, 268 BC, 293.62, 306.7 E, 326.33, 326.5 M

[56] References Cited
UNITED STATES PATENTS

| | | | |
|---|---|---|---|
| 3,567,737 | 3/1971 | Lednicer | 260/326.5 |
| 3,721,675 | 3/1973 | Mallard | 260/293.62 |
| 3,813,430 | 5/1974 | Phillips | 260/479 R |
| 3,850,935 | 11/1974 | Nakao et al. | 260/293.52 |
| 3,894,002 | 7/1975 | MacKenzie et al. | 260/239 B |

*Primary Examiner*—G. Thomas Todd
*Attorney, Agent, or Firm*—Connolly and Hutz

[57] ABSTRACT

Compounds of the formula

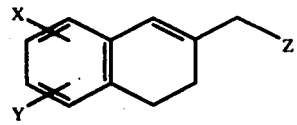

and pharmaceutically acceptable salts thereof, wherein X and Y are independently H, F, Cl, Br, alkyl having up to four carbons, or alkoxy having up to four carbons, but X and Y are not both H, and Z is a secondary or tertiary amino group, are useful as analgesics and tranquillizing agents for mammals.

9 Claims, No Drawings

2-AMINOMETHYL-3,4-DIHYDRONAPHTHALENES

BACKGROUND OF THE INVENTION

Prior investigations toward developing analgesics and similar pharmaceuticals with dihydronaphthalene structures have not been too successful. Thus A. L. Morrison and H. Rinderknecht in *Journal of the Chemical Society* 1950, pages 1510–1513, described the preparation of several proposed analgesics and referred to similar preparations by J. Lee, A. Ziering, L. Berger and J. D. Heineman in Jubilee volume Emil Barell, 1946, pages 264–305, but no very significant analgesic seems to have resulted. Indeed the Morrison et al report states that their pharmacological results "will be reported elsewhere", but no such further report seems to have been published.

U.S. Pat. Nos. 3,262,975 and 3,862,232 also refer to dihydronaphthalene structures for pharmaceutical use, but these have not made much of an impression. C. Mannich, F. Borokowsky & W. Lin in *Arch. Pharm.*, Volume 275, pages 54–62 (1937) describe some similar dihydronaphthalenes but make no mention of pharmaceutical use.

Among the objects of the present invention is the provision of novel analgesic and tranquilizing treatments, as well as novel chemicals useful in such treatment.

The foregoing as well as additional objects of the present invention will be more fully understood from the following description of several of its embodiments.

DETAILED DESCRIPTION OF INVENTION

According to the present invention the sensitivity of a mammal to external influences such as pain and anxiety causing conditions can be reduced by internally administering to the mammal a therapeutically effective amount of at least one compound having the formula

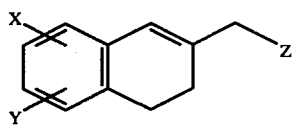

and pharmaceutically acceptable salts thereof, wherein X and Y are independently H, F. Cl, Br, alkyl having up to four carbons, or alkoxy having up to four carbons, but X and Y are not both H, and Z is a secondary or tertiary amino group.

Especially effective analgesics and tranquilizing agents useful in the treatment of mammals are those compounds of the formula

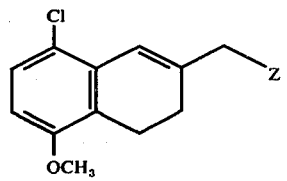

wherein Z is as defined above.

The present invention also provides methods for tranquilizing and inducing analgesia in mammals by administering a therapeutically effective amount of at least one compound of the invention.

Many of the foregoing compounds can be prepared by methods that are obvious to those skilled in the art. The preparation of

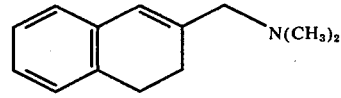

is described in the above-cited Mannich et al publication. Preferred compounds of the present invention have chloro and methoxy substitution in the aromatic ring and can be made as indicated in the following examples.

EXAMPLE 1

3-(5-Chloro-2-methoxybenzoyl)propionic Acid

A dry flask was charged with 650 ml. each of nitrobenzene and sym-tetrachloroethane, 104 g. (1.04 moles) succinic anhydride and 130 g. (0.913 mole) p-chloroanisole. The mixture was stirred at 5° C and 276 g. (2.07 moles) of anhydrous $AlCl_3$ was added portionwise over a 90 minute period such that the temperature did not exceed 10° C. The resulting mixture was stirred under nitrogen for 5 days at 7° C and then poured into a mixture of 1 kg. of ice and 176 ml. concentrated hydrochloric acid. The thus quenched mixture was steam distilled until all organic solvents were removed. The residual aqueous-oil combination was cooled to 20° C whereupon the oil phase crystallized. The aqueous supernate was then drawn off and one liter of methylene chloride was added to the remaining crystallized solid mass. The resulting slurry was warmed at 25° C with stirring, and then filtered, and the filtered-off solids washed with $CH_2Cl_2$. Upon drying of the washed solids, 84.4 g. of 3-(5-chloro-2-hydroxybenzoyl) propionic acid, m.p. 178°–182° C, was obtained.

The methylene chloride filtrate and washings were concentrated in vacuo, hexane being continually added gradually. When most of the $CH_2Cl_2$ had been evaporated, crystalline material separated. The resulting hexane slurry was cooled to 10° C and filtered, the cake washed with hexane and air dried to afford 48.7 g. of the title compound, m.p. 113°–115° C.

The higher melting 2-hydroxy compound, (84.4 g. − 0.37 mole) recovered first was mixed with 500 ml. of water and 60.9 g. (1.52 moles) sodium hydroxide. After stirring at 90°–100° C for 90 minutes, the mixture was cooled to 10° C and stirred as 126 g. (1.0 mole) of dimethyl sulfate was added in one portion. The mixture was reheated to 90°–100° C and maintained at that temperature for 4 hours. After again cooling to room temperature, an additional 60.9 g. of NaOH, 200 ml. water and 40 g. dimethyl sulfate were added and the mixture stirred overnight at 90°–100° C. Once more the mixture was cooled and water was added to bring the total volume to about 2 liters. The resulting clear red alkaline solution was chilled by addition of 500 g. of ice, then made strongly acidic with concentrated $H_2SO_4$ while keeping the temperature below 10° C. This chilled mixture was extracted with methylene chloride, and the extracts concentrated in vacuo, hexane being continually added gradually to precipitate more of the title compound. The resulting hexane slurry was cooled, filtered and washed with hexane to give an additional 74 g. of the title compound, m.p. 112°–115° C. Total yield — 55%.

When the procedure of Example 1 is repeated with the appropriately substituted benzenes, the following compounds were obtained:

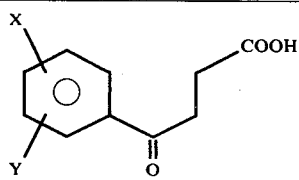

| X | Y | M.P.,°C. | % Yield |
|---|---|---|---|
| 8-F | 5-OCH₃ | 120–122 | 90 |
| 8-OCH₃ | 5-OCH₃ | 94–97 | 88 |
| 8-CH₃ | 5-OCH₃ | 89–94 | 16 |
| 7-OCH₃ | 6-OCH₃ | 154–155 | 68 |

EXAMPLE 2

4-(5-Chloro-2-methoxyphenyl)butyric Acid

In a three liter flask was charged 272 g. (4.16 gram atoms) of moxxy zinc, 400 ml. of water and 27.2 g. (0.10 mole) mercuric chloride. The flast was evacuated and its atmosphere replaced with nitrogen. When a complete nitrogen atmosphere was assured, 14.2 ml. of concentrated hydrochloric acid was added, with stirring, from a dropping funnel. The mixture was stirred for 15 minutes, and the liquid layer then siphoned out while carefully maintaining the nitrogen atmosphere in the vessel. The aqueous mixture was discarded and the flask charged with 200 ml. water, 288 ml. toluene, 16.1 ml. glacial acetic acid and 136 g. (0.56 mole) of 3-(5-chloro-2-methoxybenzoyl) propionic acid. With stirring, 495 ml. concentrated hydrochloric acid was added and while still under nitrogen, the mixture was heated to 90° C. After 3 hours an additional 140 ml. of concentrated HCl was added. This addition was repeated after 6 hours and again 18 hours of stirring, keeping the mixture at 85°–90° C at all times. After 24 hours the reaction liquid was drawn off from the remaining zinc amalgam and diluted with an equal volume of water and 750 ml. of ethyl acetate. The layers of the resulting two-phase liquid were separated and the aqueous layer extracted with an additional 350 ml. of ethyl acetate. The combined organic extracts were backwashed with water and concentrated in vacuo to an oil.

The crude oil thus obtained was taken up in 100 ml. of warm acetonitrile and this solution stirred at −5° C for 2 hours. The resulting slurry was filtered and dried in air to give 74.3 g. of the title product, m.p. 79°–81° C (58% yield).

When the preparation of Example 2 is repeated with the appropriate starting material selected as before, the following compounds were obtained:

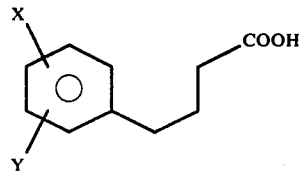

| X | Y | M.P.,°C. | % Yield |
|---|---|---|---|
| 8-F | 5-OCH₃ | 68–70 | 80 |
| 8-OCH₃ | 5-OCH₃ | oil | 70 |
| 8-CH₃ | 5-OCH₃ | oil | 100 |
| 7-OCH₃ | 6-OCH₃ | 52–53 | 99 |

EXAMPLE 3

8-Chloro-5-methoxy-1-tetralone

A flask containing 1600 g. of polyphosphoric acid and 160 g. (0.70 mole) 4-(5-chloro-2-methoxyphenyl)-butyric acid was heated on a steam bath (internal temperature 90°–95° C) for 1.5 hours. The hot reaction mixture was then poured onto 2 liters of crushed ice with stirring. The quenched mixture was stirred for 30 minutes, then extracted 3 times with 500 ml. portions of chloroform, the extract carbon treated, dried with MgSO₄ and filtered. The filtrate was concentrated in vacuo to afford 146 g. of dark oil. This was dissolved in ether, washed with aqueous NaHCO₃, then water, carbon treated, dried over MgSO₄ and evaporated to dryness. The oil thus produced was distilled under high vacuum to obtain 65.4 g. of product (44% yield). Upon cooling the distillate it crystallized, m.p. 46°–48° C.

When the procedure of Example 3 was repeated with each of the alternative products as indicated, the following 1-tetralones were obtained:

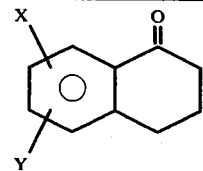

| X | Y | M.P.,°C. | % Yield |
|---|---|---|---|
| 8-F | 5-OCH₃ | 81–83 | 83 |
| 8-OCH₃ | 5-OCH₃ | 58–59 | 89 |
| 8-CH₃ | 5-OCH₃ | b.p.120° (0.3 mm.) | 78 |
| 7-OCH₃ | 6-OCH₃ | 93–94.5 | 74 |

EXAMPLE 4

1-(2-[1,2,3,4-Tetrahydro-8-chloro-5-methoxy-1-oxonaphthyl]-methyl)pyrrolidine 8-Chloro-5-methoxy-1-tetralone (7.0 g., 33 millimole) paraformaldehyde (2.04 g., 67 millimole) and pyrrolidine (2.44 ml., 28 millimole) were combined in 20 ml. of isopropanol and sufficient isopropanolic hydrogen chloride was added to adjust the solution to an acid pH. The mixture was then stirred and heated at reflux for 19 hours. Upon cooling to room temperature solid precipitated and was filtered off and washed well with isopropanol and with ether and then air dried to afford 9.3 g. (76% yield) of the hydrochloric salt of the title compound, m.p. 177°–178.5° C. This material was dissolved in 50 ml. of CHCl₃, carbon treated, filtered, and then 10 ml. of acetone was added to the filtrate. Upon then cooling in ice, 4.4 grams of the title compound (crystals — m.p. 183°–184° C) formed. Upon work-up of the mother liquor by vaporization, an additional 4.5 g. of such crystals was obtained.

By repeating the procedure of Example 4 with the appropriate starting materials in each case the following compounds were obtained:

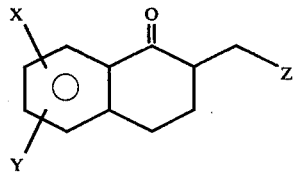

| X | Y | Z | % Yield | M.p.,°C |
|---|---|---|---|---|
| 8-Cl | 5-OCH₃ | morpholino | 20 | 172–173 |
| 8-F | 5-OCH₃ | pyrrolidyl | 76 | 58–59 |
| 8-F | 5-OCH₃ | morpholino | 79 | 89.5–91.5 |
| 8-OCH₃ | 5-OCH₃ | pyrrolidyl | 83 | 95–96 |
| 8-OCH₃ | 5-OCH₃ | morpholino | 83.5 | 103–105 |
| 8-CH₃ | 5-OCH₃ | pyrrolidyl | 60 | 180–181* |
| 8-CH₃ | 5-OCH₃ | morpholino | 65.5 | 172–173* |
| 7-CH₂CH₃ | H | pyrrolidyl | 73 | 160–161* |
| 7-CH₂CH₃ | H | morpholino | 94 | 158–159* |
| 7-CH₃ | 5-CH₃ | pyrrolidyl | 33 | 164–165* |
| 7-CH₃ | 5-CH₃ | morpholino | 71 | 183–184* |
| 6-OCH(CH₃)₂ | H | pyrrolidyl | 87.5 | 157.5–158.5* |
| 5-OCH₃ | H | pyrrolidyl | 76 | 187–188* |
| 6-OCH₃ | H | pyrrolidyl | 88 | 190–191* |
| 6-OCH₃ | H | morpholino | 78 | 62–63 |
| 7-OCH₃ | H | pyrrolidyl | 79 | 59.5–60.5 |
| 7-OCH₃ | H | morpholino | 88 | 72–73 |
| 7-OCH₃ | 6-OCH₃ | pyrrolidyl | 83.5 | 93–94.5 |
| 7-OCH₃ | 6-OCH₃ | morpholino | 72 | 178–179* |

* Hydrochloride salt

EXAMPLE 5

1-(2-[1,2,3,4-Tetrahydro-8-chloro-5-methoxy-1-hydroxynaphthyl]-methyl)pyrrolidine 8-Chloro-2-(1-pyrrolidinomethyl)-5-methoxy-1-tetralone hydrochloride (90 g., 0.27 mole) was converted to free base by suspending the solid in a mixture of ether and water and adjusting the pH of the aqueous phase to 11.5–12.5 with 10° NaOH. The organic layer was separated and combined with two additional ether extracts of the aqueous phase. The combined extracts were dried (MgSO₄) and filtered to afford 500 ml. of ether solution containing the free base.

In a dry, 3-liter, three-necked flask fitted with mechanical stirrer, condenser, dropping funnel and nitrogen inlet, was placed 1 liter of dry ether and 21 g. (0.54 mole) of lithium aluminum hydride. The mixture was refluxed gently as the above-prepared free base solution was added dropwise over about one hour. The mixture was then refluxed for an additional 3.5 hours and stirred at ambient temperature overnight. The reaction mixture was then cooled in an ice bath and stirred vigorously during the dropwise addition of 21 ml. water followed by 21 ml. of 15% sodium hydroxide solution and finally an additional 63 ml. water. The ice bath was removed and the mixture stirred for another 30 minutes. The white solid which had precipitated was collected by filtration from the resulting mixture, and triturated twice with warm ether. The ethereal filtrate was combined with the washings and the solvent evaporated to yield a white solid residue. The residue was taken up in an ether-water mixture, the pH of the aqueous phase adjusted to 2.0 with 10% hydrochloric acid, and then separated, made alkaline (pH 12.5) with 10° NaOh, and extracted three times with fresh ether. The combined final ether layers were dried over MgSO₄ and ether evaporated to afford 79 g. (89% yield) of a mixture of the cis and trans isomers of the title compound, m.p. 102°–110° C.

EXAMPLE 6

1-(2-[3,4-Dihydro-8-chloro-5-methoxynaphthyl]methyl)pyrrolidine

The product of Example 5 (79 g., 0.24 mole) was dissolved in 250 ml. of 48% hydrobromic acid after which 22 ml. of water was added. In a few minutes the reaction mixture became cloudy and a heavy white precipitate formed. The mixture was stirred at ambient temperature overnight, then 2 volumes of water were added and the precipitate collected by filtration, washed with water and sucked dry to obtain about 100 g. of wet 8-chloro-1-bromo-5-methoxy-2-(1-pyrrolidinomethyl)-3,4-dihydronaphthalene hydrobromide. An analytically pure sample melted at 219°–220° C.

The wet bromo compound was slurried in 800 ml. of acetonitrile and heated at reflux until the solid was dissolved. The solution was then concentrated to about 400 ml. and cooled. White needles of the hydromide of the title compound formed and were removed by filtration and dried to obtain 61 g., m.p. 253°–255° C (71% yield).

Anal. Calc'd for $C_{16}$ $H_{20}NOCl.HBr$ (percent): C, 53.57; H, 5.90; N, 3.91. Found (percent): C, 53.95; H, 5.89; N, 3.81.

By use of the procedures of Examples 5 and 6 the alternate intermediate products of Example 4 were reacted to give the following final products. Unless noted otherwise melting points given are for the hydrochloride salts.

|   |   |   | % Yield | | M.p.,°C. of Product | |
|---|---|---|---|---|---|---|
| X | Y | Z⁺ | Step A | Step B | Step A | Step B |
| 8-F | 5-OCH₃ | P | 95 | 66 | 196–197 | 235.5–236.5 |
| 8-F | 5-OCH₃ | M | 88 | 70 | 195–196.5 | 249.5–250.5 |
| 8-OCH₃ | 5-OCH₃ | P | 84 | 40 | 154–155 | 184–184.5 |
| 8-OCH₃ | 5-OCH₃ | M | 98 | 47 | 166–167.5 | 218–219 |
| 8-CH₃ | 5-OCH₃ | P | 93 | 63 | 167–168 | 200.5–201.5 |

-continued

| X | Y | Z+ | % Yield Step A | % Yield Step B | M.p.,°C. of Product Step A | M.p.,°C. of Product Step B |
|---|---|---|---|---|---|---|
| 8-$CH_3$ | 5-$OCH_3$ | M | 82 | 76 | 242–243 | 244–245 |
| 7-$CH_2CH_3$ | H | P | 90 | 65 | 187–188 | 220–222 |
| 7-$CH_2CH_3$ | H | M | 89 | 78 | 224–225 | 245.5–247.5 |
| 7-$CH_3$ | 5-$CH_3$ | P | 87 | 89 | 99.0–99.5* | 211–213 |
| 7-$CH_3$ | 5-$CH_3$ | M | 90 | 77 | 216–218 | 229–231 |
| 6-$OCH(CH_3)_2$ | H | P | 83 | 85 | 214.5–215.5 | 214–215 |
| 5-$OCH_3$ | H | P | 82 | 85 | 201–204 | 220–223** |
| 6-$OCH_3$ | H | P | 93 | 70 | 223.5–224.5 | 224–225 |
| 6-$OCH_3$ | H | M | 84 | 75 | 215–216 | 221–222 |
| 7-$OCH_3$ | H | P | 89 | 27 | 174–175 | 200–202 |
| 7-$OCH_3$ | H | M | 86 | 40 | 191–192.5 | 237–238 |
| 7-$OCH_3$ | 6-$OCH_3$ | P | 88 | 76 | 136–137.5 | 229–230 |
| 7-$OCH_3$ | 6-$OCH_3$ | M | 71 | 88 | 227.5228.5 | 224.5–225.5 |

+P=Pyrrolidyl
M=Morpholino
*Melting point given is for free base.
**Melting point given is for HBr salt.

EXAMPLE 7

1-(2-[3,4-Dihydro-8-chloro-5-methoxynaphthyl]methyl)pyrrolidine

An alternate method of dehydrating the tetrahydronaphthols is provided by the procedure of Stone et al, J. Med. Chem., 8, 829 (1965). o-Sulfobenzoic anhydride (332 mg., 1.8 millimole) and 1-(2-[1,2,3,4-tetrahydro-8-chloro-5-methoxy-1-hydroxynaphthyl]methyl)pyrrolidine (264 mg., 0.9 millimole) were dissolved in 10 ml. of glacial acetic acid. The reaction mixture was refluxed for about 18 hours, then cooled, poured onto ice and its pH adjusted to about 10 with 20% sodium hydroxide solution. The resulting mixture was extracted with methylene chloride, and the extract backwashed with brine and dried over $MgSO_4$. After filtering and removal of the extracting solvent by evaporation in vacuo, 212 mg. of clear oil was obtained from the extract. The oil was dissolved in a mixture of ether and isopropanol and dry hydrogen chloride gas was passed through the solution. White solid precipitated and was collected by filtration and dried to obtain the hydrochloride salt of the title compound, m.p. 234°–236° (70% yield). Identity was ascertained by comparison of infrared, mass spectra, and ultraviolet spectral data with that of authentic material.

EXAMPLE 8

8-Chloro-5-methoxy-2-chloromethyl-3,4-dihydronaphthalene 1-(2-[3,4-Dihydro-8-chloro-5-methoxynaphthyl]methyl) pyrrolidine free base (56 g., 0.202 mole) and phenylchloroformate (37 g., 0.23 mole) were combined in methylene chloride and stirred at reflux for 2.5 hours. The reaction mixture was then cooled, washed with dilute hydrochloric acid, with dilute bicarbonate solution and with 50 ml. of saturated NaCl solution, dried over $MgSO_4$ and evaporated to dryness in vacuo to obtain 79.6 g. of pale yellow oil. The oil was passed through a 4 × 30 cm. silica gel column containing about 300 ml. of silica. Elution was carried out with 1:1 benzene-hexane taking 150 ml. fractions. The produce was concentrated in the first 5 fractions. These fractions were combined and the solvent evaporated in vacuo to obtain 29.8 g. of the title compound as a colorless product, m.p. 68°–69.5° C (61% yield).

EXAMPLE 9

1-(2-[3,4-Dihydro-8-chloro-5-methoxy]naphthyl)-methyl-3-hydroxypiperidine

3-Hydroxypiperidine (416 mg., 4.2 millimole), 8-chloro-5-methoxy-2-chloromethyl-3,4-dihydronaphthalene (1.0 g., 4.12 millimole) and 1.3 g. (16 millimole) sodium bicarbonate were combined with 10 ml. of dry dimethylformamide. The resulting mixture was heated at 60° C for 10 minutes then allowed to cool to ambient temperature and stand overnight. The reaction mixture was then filtered to remove insoluble material, the filtrate diluted with 100 ml. of 1-Normal hydrochloric acid and extracted with three 25 ml. portions of ether. The extracts were discarded and the aqueous phase was made alkaline with 10% aqueous NaOH. Extraction was then carried out with three 30 ml. portions of fresh ether, the organic layers were combined, washed twice with 10 ml. portions of water, then with 50 ml. saturated NaCl solution, dried over $MgSO_4$, filtered and evaporated to dryness to leave an oil residue. This was dissolved in 5 ml. of ethanol, 5 ml. of ether was added, and the pH of the mixture was adjusted to about 1 by addition of a solution of anhydrous hydrogen chloride in isopropanol. After stirring for 15 minutes, the hydrochloride salt that precipitated was collected on a filter, washed with isopropanol, then ether, and air dried to afford 1.94 g. of the hydrochloride of the title compound as a tan solid. An additional 42 mg. was obtained from the mother liquor, total yield 73%, m.p. 212.5°–214.5° C.

Anal. Calc'd for $C_{17}H_{22}NO_2Cl.HCl$ (percent): C, 59.30; H, 6.73; N, 4.07. Found (percent): C, 59.09; H, 6.72; N, 4.09.

By repeating the procedure of Example 8 but employing in each case, an equivalent amount of the appropriate amine in place of 3-hydroxypiperidine, the following compounds were obtained. The melting points listed are for the free base unless otherwise noted.

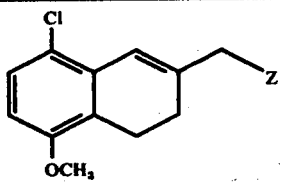

| Z | Yield | M.p.° C. | Solvent for Crystallization |
|---|---|---|---|
| —N⟨piperidine⟩—OH | 17 | 75 | Isopropanol-ethyl acetate |
| —N⟨thiazolidine⟩S | 62 | 205–207* | Isopropanol-MeOH |
| —N⟨piperidine⟩—CONH₂ (3-) | 46+ | 124–126 | acetone |
| —N⟨piperidine⟩—CONH₂ (4-) | 37+ | 138–140 | ether |
| —N⟨piperidine⟩—CONHCH₃ | 25+ | 176–181 | ethylacetate-isopropanol |
| —N⟨piperidine⟩—CON(CH₃)₂ | 5+ | 198–200** | isopropanol |
| —N⟨piperidine⟩—CON⟨pyrrolidine⟩ | 30+ | 128–133** | Ether-acetone |
| —N⟨piperidine⟩—CONH—C₆H₁₁ | 62+ | 171–172 | Ethyl acetate |
| —N⟨piperazine⟩NSO₂NH₂ | 23+ | 189–192** | Ether |
| —N⟨pyrrolidine⟩(C₆H₅)(OH) | 60 | 146–147** | Isopropanol-ether |
| —N⟨piperidine⟩(C₆H₅)(COCH₃) | 82 | 117–120 | Ether |
| —N⟨piperidine⟩(C₆H₅)(CON⟨pyrrolidine⟩) | 25+ | 234–236 | CHCl₃ |

-continued

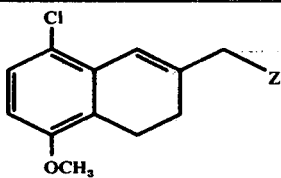

| Z | Yield | M.p.° C. | Solvent for Crystallization |
|---|---|---|---|
| [piperidine-N-C(=O)-NH-phenyl fused ring] | 62+ | 212–218 | Ether |
| [piperidine-CON-piperazine-N-CH₃] | 31+ | 78–80 | Hexane |
| [piperidine-CON-morpholine] | 64+ | 132–136 | Hexane |
| [piperidine with C(OH)(4-Cl-phenyl)] | 63+ | 242–243++ | Isopropanol |
| [piperidine-NHCON-piperidine] | 53 | 228–229 | Isopropanol-ethyl acetate |
| [piperidine with N-piperidine and CONH₂] | 60+ | 181–182 | Ethanol |
| [piperidine-CON-piperidine] | | 128–132 | Ethylacetate-ether |
| [spiro structure with N-CH₃ and C₆H₅] | | 175–178 | Ether |

+Reaction carried out in ethanol as solvent.
*Hydrochloride hydrate (. HCl . H₂O)
**Hydrochloride addition salt (. HCl)
++Sulfuric acid addition salt (. H₂SO₄)

Similar results are obtained when the appropriate amines are used to provide the following Z components:

| Z |
|---|
| —NHCH(CH₃)₂ |
| —NH(CH₂)₃CH₃ |
| —NH—CH₂CH =CHCH₃ |

-continued

| Z |
|---|
| —NHCH₂CH=CH(CH₂)₃CH₃ |
| —NH—CH—CH₂CH₂ (cyclic) |
| —NH—CH—(CH₂)₃—CH₂ (cyclic) |
| —NHCH—(CH₂)₄CH₂ (cyclic) |
| —NCH(CH₂)₄CH₂ (cyclic)<br>  CH₃ |
| —N(CH₂CH₂CH₃)₂ |
| —N(CH₂CH₂CH₂CH₃)₂ |
| —NHCH₂CH—CH₂CH₂CH₂ (cyclic) |
| —NHCH₂CH(CH₂)₄CH₂ (cyclic) |
| —NHCH₂CH₂NCH₂(CH₂)₃CH₂ (cyclic) |

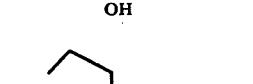

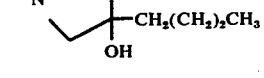

—NHCH₂CH₂OCH₂CH₃
—NHCH₂CH₂OCH₂(CH₂)₂CH₃
—NHCH₂CH₂OCH₂(CH₂)₂CH₃
3-Hydroxypyrrolidino

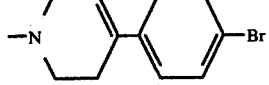

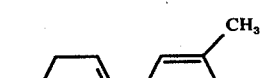

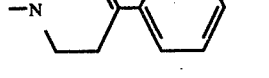

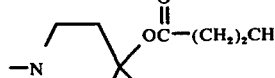

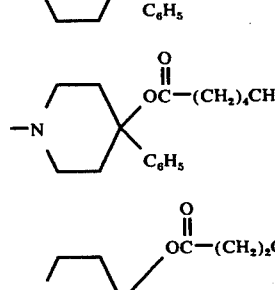

-continued

| Z |
|---|
| 4-(2-butenyl)piperazino |
| 4-(1-heptenyl)piperazino |
| 4-methoxycarbonylpiperazino |
| 4-amyloxycarbonylpiperazino |
| 4-(4-bromophenyl)piperazino |
| 4-(2-methylphenyl)piperazino |
| Dimethylamino |
| Piperidino |
| 4-ethylpiperidino |
| 4-butylpiperidino |
| 4-allylpiperidino |
| 4-(2-butenyl)piperidino |
| 4-(2-pentenyl)piperidino |
| 4-methoxypiperidino |
| 4-isopropoxypiperidino |
| 4-n-butoxypiperidino |
| 4-n-hexanoyloxypiperidino |
| 4-propionylpiperidino |
| 4-butyroylpiperidino |
| 4-n-butylaminocarbonyl-piperidino |
| 4-di-n-butylaminocarbonyl-piperidino |
| 4-morpholinopiperidino |
| 4-cyclopropylaminocarbonyl-piperidino |
| 4-cyclopentylaminocarbonyl-piperidino |
| 4-(3-bromophenyl)piperidino |
| 4-(4-methoxyphenyl)piperidino |
| 4-(3-methylphenyl)piperidino |
| 4-(2-trifluoromethylphenyl)-piperidino |
| 4-ethylpiperazino |
| 4-(2-ethyl)butylpiperazino |

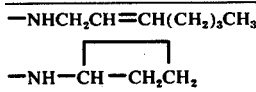

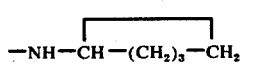

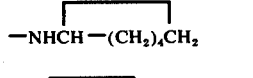

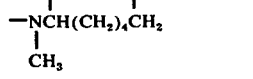

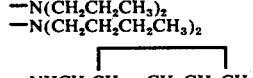

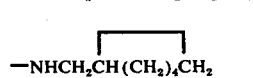

-continued

Z

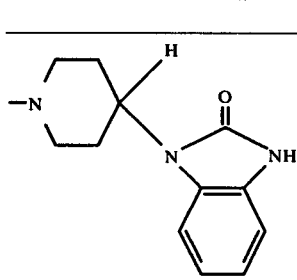

EXAMPLE 10

The analgesic activity of the compounds of the invention was demonstrated by their effectiveness in one or more of the following tests:

A. Rat Jump — the supression of the "jump" component of the Flinch, Squeak and Jump Test of Evans, Psychopharmacologia, 2, 318–325 (1961); see also Tenen, Psychopharmacologia, 12, 278–285 (1968). Here a modification of the Evans (1961) flinch-jump procedure is used for measuring "pain thresholds". Rats of 210–270 grams weight are placed in a chamber and presented with a series of 1-second electrical foot shocks in increasing intensity. These intensities are 0.1, 0.2, 0.3, 0.4, 0.6, 0.8, 1.2, 1.6 and 2.2 milliamperes. The shocks are presented at 30-second intervals and the animal's behavior is rated by the current at which it first jumps (animal moves forward or jumps forward). Control rats generally respond at 0.6 milliamperes.

B. Hot Plate Test of Eddy and Leimback, J. Pharm. Exp. Ther., 107, 385 (1953). Here an aluminum plate is heated to 55° C ±0.2° by an electrically-controlled infrared heat lamp. When placed on the hot plate mice normally raise or kick the hind limbs after about 5 seconds. The criterion of "analgesia" is failure to exhibit the characteristic hind limb response within 10 seconds, and the percentage noted of the number of mice tested that showed such analgesia.

C. Tail Flick Test of Witkin et al, Proc. Soc. Exp. Biol. 101, 377 (1959). Here mice are inserted into cylindrical metal restraints with tails protruding. A high intensity heat source is focused on the tail. Latency of tail flick, normally about 5 seconds, is noted, and any latency exceeding 10 seconds meets the criterion of "analgesia". Again the percentage of analgesia response was noted.

D. Mouse Tail Pinch — a modification of the procedure of Haffner, Deutsche Med. Wochenschrifte, 55, 731–732 (1929). Here the mice are strongly pinched on the base of the tail. An audible squeak is taken as indication of analgesic activity in drugged mice. Here too the percentage of the tested mice showing analgesia was noted.

In the tests the designated compounds of the present invention, having the formula,

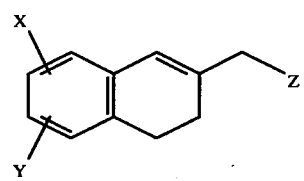

were administered intraperitoneally (IP) as a suspension in isotonic saline water at a dosage of 32 mg./kg for the Rat Jump Test and 100 milligrams per kilogram for the other tests. In each of the test figures are given for the test results 0.5 hour after and also 2.0 hours after administration of the test compound. This group of tests is considered to have very good correlation with response in humans.

The tabulated test results include comments regarding toxicity and adverse effects noted with certain compounds.

| X | Y | Z | Rat Jump .5 hr | 2 hr | Hot Plate .5 hr | 2 hr | Tail Flick .5 hr | 2 hr | Tail Pinch .5 hr | 2 hr | Comments |
|---|---|---|---|---|---|---|---|---|---|---|---|
| 8-Cl | 5-OCH$_3$ | pyrrolidino | 1.2 (2.2) | 2.2 | 80 | 0 | 60 | 0 | 20 | 0 | — |
| 8-Cl | 5-OCH$_3$ | —N(CH$_3$)$_2$ | 1.2 | 0.6 | 0 | 0 | 0 | 0 | 0 | 0 | — |
| 8-Cl | 5-OCH$_3$ | piperidine-OCCH$_2$CH$_3$ | 1.2 | 1.2 | 0 | 0 | 20 | 0 | 0 | 0 | — |
| 8-Cl | 5-OCH$_3$ | piperidine-OH, H | 1.2 | 1.2 | 0 | 0 | 0 | 0 | 0 | 0 | — |
| 8-Cl | 5-OCH$_3$ | piperidine-CONH$_2$, H | 0.6 | 0.6 | 90 | 70 | 70 | 0 | 0 | 0 | — |
| 8-Cl | 5-OCH$_3$ | piperidine-imidazolidinone-NCH$_3$, C$_6$H$_5$ | 1.2 | 1.2 | 20 | 0 | 0 | 0 | 0 | 0 | — |

-continued
| X | Y | Z | Rat Jump .5 hr | Rat Jump 2 hr | Hot Plate .5 hr | Hot Plate 2 hr | Tail Flick .5 hr | Tail Flick 2 hr | Tail Pinch .5 hr | Tail Pinch 2 hr | Comments |
|---|---|---|---|---|---|---|---|---|---|---|---|
| 8-Cl | 5-OCH₃ | 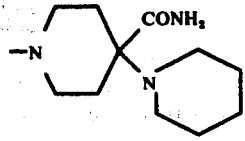 | 1.2 | 1.6 | | | | | | | |
| 8-Cl | 5-OCH₃ |  | 1.2 | 1.2 | 10 | 0 | 0 | 0 | 0 | 0 | — |
| 8-Cl | 5-MeO | 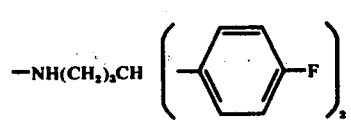 | 1.2 | 1.2 | 0 | 0 | 0 | 0 | 0 | 0 | — |
| 8-Cl | 5-MeO | 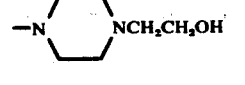 | 1.2 | 1.2 | 50 | 20 | 10 | 0 | 40 | 0 | — |
| 8-Cl | 5-MeO |  | 1.2 | 1.2 | 50 | 0 | 30 | 0 | 0 | 0 | — |
| 8-Cl | 5-MeO | 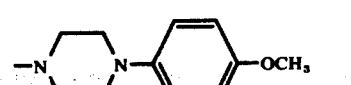 | 1.2 | 1.2 | 0 | 0 | 0 | 0 | 0 | 0 | — |
| 8-Cl | 5-MeO |  | 1.2 | 1.2 | 70 | 40 | 40 | 0 | 0 | 0 | — |
| 8-Cl | 5-MeO |  | 1.2 | 1.2 | 60 | 0 | 40 | 0 | 0 | 0 | — |
| 8-Cl | 5-MeO | 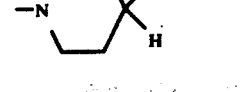 | 1.2 | 1.2 | 25 | 0 | 25 | 0 | 0 | 0 | 1/5 mice died at 32 mg./kg. |
| 8-Cl | 5-MeO |  | 1.6 | 2.2 | 0 | 0 | 0 | 0 | 0 | 0 | |
| 8-Cl | 5-OCH₃ | 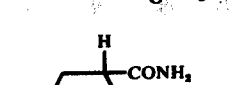 | 1.6 | 1.2 | 20 | 0 | 40 | 0 | 0 | 0 | loss of righting reflex in 2/5 rats at 100 mg./kg. |
| 8-Cl | 5-OCH₃ | 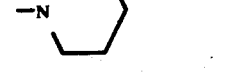 | 1.2 | 1.6 | 20 | 0 | 0 | 0 | 0 | 0 | — |

-continued

| X | Y | Z | Rat Jump .5 hr | 2 hr | Hot Plate .5 hr | 2 hr | Tail Flick .5 hr | 2 hr | Tail Pinch .5 hr | 2 hr | Comments |
|---|---|---|---|---|---|---|---|---|---|---|---|
| 8-Cl | 5-OCH$_3$ | —N⟨piperidine⟩—NHC(O)—N⟨piperidine⟩ | 1.2 | 1.2 | 0 | 0 | 0 | 0 | 0 | 0 | loss of righting reflex in 1/5 rats at 100 mg./kg. |
| 8-Cl | 5-OCH$_3$ | —N⟨piperazine⟩N—CH$_3$ | 1.2 | 1.2 | 60 | 0 | 30 | 0 | 80 | 0 | — |
| 8-Cl | 5-OCH$_3$ | —N⟨piperazine⟩N—C$_6$H$_4$Cl | 1.2 | 1.2 | 10 | 0 | 0 | 0 | 0 | 0 | — |
| 8-Cl | 5-OCH$_3$ | —N⟨piperidine with OCH$_2$CH$_3$, C$_6$H$_5$⟩ | 1.2 | 1.2 | 50 | 0 | 10 | 0 | 0 | 20 | — |
| 8-Cl | 5-OCH$_3$ | —N⟨piperidine⟩—C$_6$H$_5$ | 1.2 | 1.2 | 30 | 0 | 0 | 0 | 0 | 0 | — |
| 8-Cl | 5-OCH$_3$ | —N⟨piperazine⟩N—C$_6$H$_4$CF$_3$ | 1.2 | 1.2 | 10 | 0 | 0 | 0 | 0 | 0 | — |
| 8-Cl | 5-OCH$_3$ | —NHCH$_2$—⟨cyclopropyl⟩ | 1.2 | 1.2 | 40 | 10 | 20 | 0 | 40 | 0 | 1/5 rats died at 32 mg./kg. |
| 8-Cl | 5-OCH$_3$ | —N(CH$_3$)—CH$_2$CH$_2$—N⟨piperidine⟩ | 1.2 | 1.2 | 0 | 0 | 0 | 0 | 0 | 0 | — |
| 8-Cl | 5-OCH$_3$ | —N⟨tetrahydropyridine⟩—C$_6$H$_4$Cl | 1.2 | 1.2 | 0 | 0 | 0 | 0 | 0 | 0 | — |
| 8-Cl | 5-OCH$_3$ | —N⟨piperidine with C$_6$H$_5$, OCOCH$_3$⟩ | >2.2 | >2.2 | 100 | 80 | 90 | 70 | 100 | 100 | — |
| 8-Cl | 5-OCH$_3$ | —N⟨thiazolidine⟩S | 1.2 | 1.2 | 0 | 0 | 0 | 0 | 0 | 0 | — |
| 8-Cl | 5-OCH$_3$ | —N⟨piperidine⟩—C(O)N(CH$_3$)$_2$ | 1.2 | 1.2 | — | — | — | — | — | — | — |
| 8-Cl | 5-OCH$_3$ | —N⟨piperidine⟩—C(O)—N⟨morpholine⟩O | 1.2 | 1.2 | — | — | — | — | — | — | — |

CONTROL DATA

| | | | | | | | | | | | |
|---|---|---|---|---|---|---|---|---|---|---|---|
| Codeine Sulfate | | | >2.2 (at 32 mg./kg.IP) | — | 80 (at 100 mg./kg.IP) | 60 | 100 | 50 | ED$_{50}$ 15.4 mg./kg. | — | |
| Morphine Sulfate | | | >2.2 (at 32 mg./kg.IP) | — | 100 (at 100 mg./kg.IP) | 100 | 100 | 100 | ED$_{50}$ 4.8 mg./kg. | — | |

-continued

| X | Y | Z | Rat Jump .5 hr 2 hr | Hot Plate .5 hr 2 hr | Tail Flick .5 hr 2 hr | Tail Pinch .5 hr 2 hr | Comments |
|---|---|---|---|---|---|---|---|
| d-Propoxyphene | | | 1.2 (at 32 mg./kg.IP) | 60 0 (at 32 mg./kg.IP) | 40 20 | $ED_{50}$ 11.5 mg./ kg. 100 mg./kg. | toxic at 100 mg./kg. |

EXAMPLE 11

The following results typify the tranquilizing activity of the compounds of the invention, and are based on amphetamine antagonism procedure of Quinton and Halliwell, Nature, 200, 178–179 (1963) as modified by Weissman et al., J. Pharmacol. Exp. Ther., 151, 339–352 (1966). The results were obtained with 200–300 g. rats using the following rating scale. Groups of five rats were placed in covered plastic cages measuring approximately 26 × 42 × 16 cm. After a brief period of acclimation in the cage, the rats in each group were administered the potential amphetamine antagonist intraperitoneally as a suspension in isotonic saline water. They were then treated 1, 5, 24 and sometimes 48 hours later with d-amphetamine sulfate, 5 mg./kg. also administered intraperitoneally. One hour after the amphetamine was given each rat was assessed for its most characteristic behavior on a 6-point scale: 0 = sleeping; 1 = alert but not moving; 2 = moving around cage; 3 = sniffing, usually directed upward at the lid of the cage; 4 = licking the wall or sawdust-covered floor of the cage; 5 = gnawing or biting the floor or walls of the cage. These ratings have been shown to represent increasing degrees of amphetamine effect. Also as pointed out by Weissman et al., this test has an excellent correlation with effectiveness in humans. To simplify quantification the ratings were converted to dosages considered as approximately neutralizing the amphetamine effect.

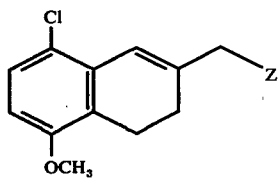

| Z | Amphetamine Antagonism Activity, mg./kg. |
|---|---|
| -N⟨pyrrolidine⟩-C₆H₅, OH | 3.2–10 |
| -N⟨piperidine⟩(OH)(C₆H₄Cl) | 0.32–1.0 |
| -N⟨piperidine⟩(OCCH₃)(C₆H₅) | <0.32 |
| -N⟨piperidine⟩(OCH₂CH₃)(C₆H₅) | 3.2–10 |
| -N⟨piperidine⟩ spiro imidazolidinone N-CH₃, N-C₆H₅ | 3.2–10 |
| -N⟨piperidine⟩(H)(CONH₂) | 3.2–10 |
| -N⟨piperidine⟩ | 10–32 |
| -N⟨morpholine⟩ | 10–32 |
| -N⟨piperidine⟩-C(O)-N⟨piperidine⟩ | 10–32 |
| -N⟨thiazolidine⟩S | 32–100 |
| Codeine sulfate | >32 |
| Morphine sulfate | 10–32 |
| Chlorpromazine | 3.2–10 |

The 1-position of the naphthalene nucleus in the compounds of the present invention seems to be a critical position inasmuch as even placing a methyl group there can prevent or radically diminish the pharmacological results achieved by the compounds of the present invention. Thus the following compound

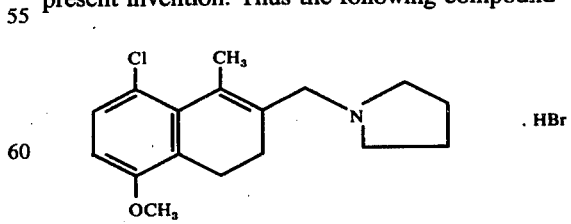

is inactive in the Rat Jump Test at a dosage of 100 milligrams per kilogram and only showed marginal activity in the Hot Plate and Tail Flick tests.

The 2-aminomethyl-3,4-dihydronaphthalenes of the present invention have varying analgesic and tranquilizing effectiveness. The greater the effectiveness per unit weight, the fewer are the side effects that can be expected. Examples 10 and 11 show that 1-(2-[5-methoxy-8-chloro-3,4-dihydronaphthyl]methyl)-4-phenyl-4-acetoxy-piperidine is of outstanding effectiveness, but the other compounds tested are also useful. The presence of a substituent in the number 1 position of the naphthalene nucleus generally deactivates or sharply lowers the effectiveness, as does the absence of any substituents on the aromatic ring of that nucleus. However the latter compounds can be fairly simply subjected to substitution reactions for conversion to the substituted compounds of the present invention, and such intermediates are desirable for this purpose.

According to the present invention, the 2-aminomethyl-3,4-dihydro-naphthalenes and their pharmaceutically acceptable salts, useful as analgesics and tranquilizing agents, are administered either as individual therapeutic agents or as mixtures of therapeutic agents. They may be administered alone, but are generally administered with a pharmaceutical carrier selected on the basis of the chosen route of administration and standard pharmaceutical practice. For example, they can be administered orally in the form of tablets or capsules containing such excipients as starch, milk sugar, or conventional types of clay, etc. They can be administered in the form of elixirs or oral suspensions with the active ingredients combined with emulsifying and/or suspending agents. They may be injected parenterally, and for this use the compounds of the invention or appropriate derivatives may be prepared in the form of sterile aqueous solutions. Such aqueous solutions should be suitably buffered, if necessary, and should contain other solutes such as saline or glucose to render them isotonic.

Although the treatment of the present invention is applicable to mammals in general, it is particularly helpful with people as well as with pets, such as dogs, cats and even horses, to help them travel in confined quarters for long periods of time. In determining the efficacious dose, results of rat and mouse testing are extrapolated on the basis of the correlation between different mammals. Also if standard analgesics or tranquilizing agents are administered effectively to humans or any mammals at any defined rate such as 100 to 400 mg. daily, similar doses will provide comparable responses for the compounds of the present invention, inasmuch as they are about as active or even more active, than standard analgesics such as d-propoxyphene and standard tranquilizing agents such as chloropromazine.

Obviously, the physician or veterinarian will ultimately determine the dosage for a particular individual or animal, and it will vary with the age, weight and response of the particular patient, as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same response level produced by a smaller quantity administered parenterally.

Having full regard for the foregoing factors, it is considered that a daily dosage of the compounds of the instant invention in humans of about ½ to 20 milligrams per kilogram of body weight or approximately 50 to 1000 mg., with a preferred range of 50 to 250 mg., are therapeutically effective. These values are illustrative, and there may, of course, be individual cases where higher or lower dose ranges are merited. The effects of such administration are generally long-lasting, and one administration every twelve to twenty-four hours is generally adequate, intraperitoneally, orally or intramuscularly. The same daily milligram per kilogram dosages, and dosage frequency is applicable to cats, dogs and horses.

The following are examples of formulations suitable for administration.

EXAMPLE 12

Tablets

A tablet base is prepared by blending the following ingredients in the proportion by weight indicated:

| | |
|---|---|
| Sucrose, U.S.P. | 80.3 |
| Tapioca starch | 13.2 |
| Magnesium stearate | 6.5 |

Into this tablet base there is blended sufficient 1-(2-[3,4-dihydro-8-chloro-5-methoxynaphthyl]methyl)-pyrrolidine hydrochloride to provide tablets containing 25, 50, 100 and 250 mg. of active ingredient per tablet. The compositions are each compressed into tablets, each weighing 500 mg.

EXAMPLE 13

Capsules

A blend is prepared containing the following ingredients:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient 1-(2-[3,4-dihydro-8-chloro-5-methoxynaphthyl]methyl)pyrollidine hydrochloride to provide capsules containing 10, 25, 50 and 100 mg. of active ingredient per capsule. The compositions are filled into conventional hard gelatin capsules in the amount of 350 mg. per capsule.

EXAMPLE 14

Suspension

A suspension of 1-(2-[3,4-dihydro-8-chloro-5-methoxynaphthyl]methyl)-4-phenyl-4-acetoxypiperidine sulfate is prepared with the following composition:

| | |
|---|---|
| Effective ingredient | 20.00 |
| 70% aqueous sorbitol | g. 741.29 |
| Glycerine, U.S.P. | g. 185.35 |
| Gum acacia (10% solution) | ml.100.00 |
| Polyvinylpyrrolidone | g. 0.50 |
| Distilled water, sufficient to make 1 liter. | |

To this suspension, various sweeteners and flavorants can be added to improve the platability of the suspension. The suspension contains approximately 20 mg. of effective agent per milliliter and is conveniently added to dogfood, catfood or horsefeed.

EXAMPLE 15

Sesame oil is sterilized by heating to 120° C. for 2 hrs. To this oil, a sufficient quantity of pulverized 1-(2-[3,4-dihydro-8-chloro-5-methoxynaphthyl]methyl)-4-methylpiperazine hydrochloride is added to make a 0.50% suspension by weight. The solid is thoroughly dispersed in the oil by use of a colloid mill, the dispersion then filtered through a 100–250 mesh screen, poured into sterile vials and sealed.

The analgesics and tranquilizing agents of the present invention can be made by processes other than those exemplified above. Thus the corresponding naphthoyl amides are readiy prepared from the 3,4-dihydronaphthalene-2-carboxylic acids which in turn are obtained by condensation of the appropriately substituted γ-phenylbutyrate ester with a lower alkyl formate ester in the presence of bases such as the alkali metal alkoxides or alkali metal and alkaline earth hydrides to form the corresponding α-formyl-γ-phenylbutyrate esters, and then cyclizing the formyl compound in the presence of dehydrating agents such as the polyphosphoric acid or concentrated sulfuric acid. The 3,4-dihydronaphthalene-2-carboxylic acids are obtained by hydrolysis of the resulting esters, and are reduced by in situ formed aluminum hydride. This entire sequence is schematically outlined as:

ester in aqueous methanolic sodium hydroxide, was added 35 ml. of thionyl chloride. The resulting mixture was heated to reflux whereupon complete solution was obtained after about 30 minutes. Reflux was continued for an additional hour, then the volatile products were removed by evaporation at reduced pressure to obtain a brown solid residue. The residue was dissolved in 50 ml. methylene chloride and a solution of 4.16 g. (0.042 mole) 4-methylpiperidine in 5.0 ml. methylene chloride was added dropwise over a 20 minute period. Upon completion of the addition the reaction mixture was allowed to stand at ambient temperature overnight. A 25 ml. increment of $CH_2Cl_2$ was then added and the solution washed with 75 ml. of 1.0N sodium hydroxide, 75 ml. 1.0N hydrochloric acid, 75 ml. water and finally with 75 ml. saturated solution of NaCl in water. The washed extracts were dried over $MgSO_4$, filtered and the solvent removed in vacuo to yield 7.0 g. of an amber-colored oil. The oil was purified by silica gel chromatography, eluting with 10% ethyl acetate 90% benzene. The fractions containing product were combined and solvent evaporated in vacuo to obtain 5.02 g. of the title compound, m.p. 93°–95° C. upon crystallization from hexane. A further 0.35 g. was obtained from the mother liquors, m.p. 92°–93.5° C. Total yield: 80%.

Anal. Calc'd for $C_{18}H_{22}NO_2Cl$ (percent): C, 67.60; H, 6.91; N, 4.39. Found (percent): C, 67.47; H, 6.84; N, 4.24.

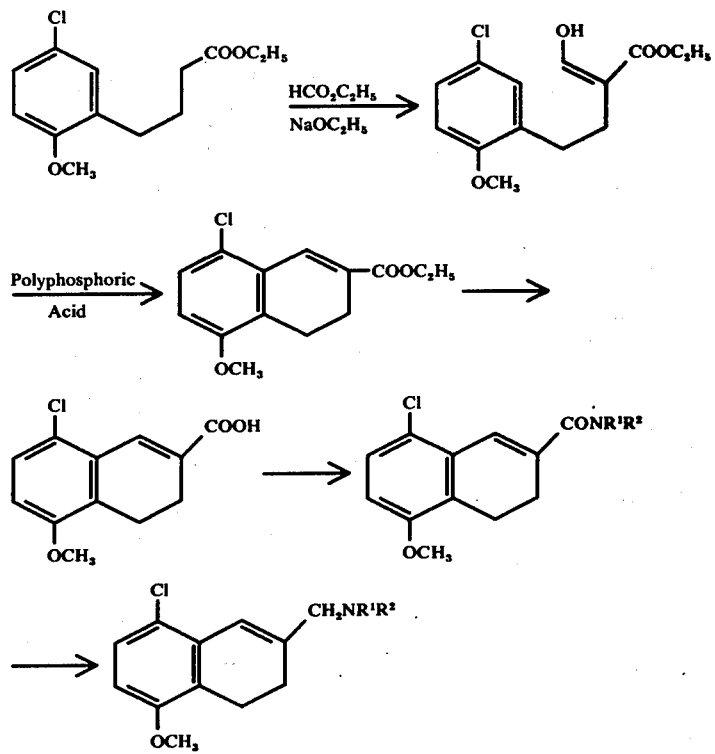

wherein $-NR^1R^2 = Z$ as defined above; and shown in part in the following examples.

EXAMPLE 16

1-(2-[3,4-Dihydro-8-chloro-5-methoxy]naphthoyl)-4-methylpiperidine

To 5.0 g. (0.021 mole) 8-chloro-5-methoxy-3,4-dihydronaphthalene-2-carboxylic acid, m.p. 217°–221° C., prepared by saponification of the corresponding ethyl

EXAMPLE 17

1-(2-[3,4-Dihydro-8-chloro-5-methoxynaphthyl]methyl)-4-methylpiperidine

Under anhydrous conditions 1.40 g (0.037 mole) lithium aluminum hydride was slurried in 50 ml. tetrahydrofuran and cooled to 0.5° C. Anhydrous aluminum chloride (1.66 g., 0.0124 mole) was added and the mixture allowed to stir for about 30 minutes. A solution of 5.0 g (0.0156 mole) of the amide prepared in Example 16 in 15 ml. tetrahydrofuran was added dropwise at 0.5° C. over 20 minutes and the mixture stirred for an additional 2 hours. The reaction mixture was quenched by cautious addition of water. A white solid precipitated and was filtered off, the filtrate being then evaporated in vacuo. The unvolatilized residue was dissolved in ethyl acetate. The filtered off precipitate was triturated with ethyl acetate, filtered and the filtrate combined with the above ethyl acetate solution. The combined organic layers were washed with water, then saturated solution of NaCl in water, and dried over $MgSO_4$, filtered and solvent removed in vacuo. The residual oil was dissolved in 75 ml. ether, and anhydrous HCl gas was bubbled through the ether solution to precipitate the hydrochloric salt of the title compound, 4.3 g., m.p. 247°–249° C.

Anal. Calc'd for $C_{18}H_{25}NOCl_2$ (percent): C, 63.16; H, 7.36; N, 4.09. Found (percent): C, 63.45; H, 7.45; N, 3.99.

EXAMPLE 18

1-(2-[3,4-dihydro-8-chloro-5-methoxy-naphthyl]methyl)-4-hydroxy-4-phenylpiperidine Under anhydrous conditions 1.95 g. (0.056 mole) lithium aluminum hydride and 2.25 g (0.0168 mole) anhydrous aluminum chloride were combined in 60 ml. of dry ether to generate aluminum hydride in situ. At ambient temperature a solution of 1-(2-[3,4-dihydro-8-chloro-5-methoxy]naphthoyl)-4-hydroxy-4-phenylpiperidine (9.0 g., 0.021 mole) in 25 ml. of tetrahydrofuran was added dropwise over about 30 minutes to the combination. The resulting mixture was stirred for an additional hour, then worked up as in the preceding example. The hydrochloride salt was precipitated from ether, m.p. 242°–243.5° C. The free base could only be obtained as a glass.

Anal. Calc'd for $C_{23}H_{26}O_2NCl$ (percent): C, 71.9; H, 6.78; N, 3.65. Found (percent): C, 70.6; H, 6.58; N, 3.46.

The same procedure produces the following compounds when starting with the corresponding amide:

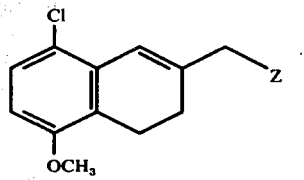

| Z | % Yield | M.P.,°C. | Solvent for Precipitation |
|---|---|---|---|
| —NHCH₃ | 61 | 184–186* | ether-ethanol |
| —NHCH₂CH=CH₂ | 45 | 213–216* | ether-ethanol |
| —NHCH—◁ | 36 | 180–187 | hexane |
| —NH—⟨S⟩ | 58 | 216–218* | ether-ethanol |
| —NH—CH₂CH₂OCH₃ | 35 | 168–171* | ether-isopropanol |
| —N⟨bicyclic⟩ | 49 | 259–262 | ether |
| —N⟨piperidine-H,C₆H₅⟩ | 75 | 94–97 | ether |
| —N⟨piperidine-C₆H₄Cl⟩ | 35 | 243–246 | ether |
| —N⟨tetrahydropyridine-C₆H₅⟩ | 34 | 125–126 | ethyl acetate-hexane |
| —N⟨piperidine-H,N-pyrrolidine⟩ | 36 | 108–109 | hexane-methylene chloride |

-continued

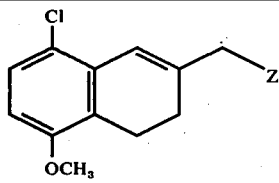

| Z | % Yield | M.P.,°C. | Solvent for Precipitation |
|---|---|---|---|
| -N(piperazine)N-C₆H₄-CF₃ | 95 | 73–76 | ether |
| -N(piperazine)N—CH₃ | 64 | 73–74 | pentane |
| -N(piperazine)N—CO₂CH₂CH₃ | 60 | 195 | tetrahydrofuran |
| -N(piperazine)N—CH₂CH₂OH | 50 | 105–109 | hexane |
| -N(CH₃)—CH₂CH₂—N(pyrrolidine) | 52 | 231–235** | ether-ethanol |
| -N(piperazine)N-C₆H₄-OCH₃ | 90 | amorphous |  |
| -N(piperazine)N-C₆H₄-Cl | 60 | 122–123 | hexane |
| -N(piperazine)N—CH₂CH=CH₂ | 57 | 258–259** (dec.) | ether |
| -N(piperidine with C₆H₅ and OCH₂CH₃) | 47 | 113–114 | hexane-methylene chloride |
| -NH—(CH₂)₃—CH(C₆H₄-F)₂ | 72 | 176–178⁺ | ether |

*. HCl Salt
**. 2HCl Salt
⁺Maleate Salt

The analgesics and tranquilizing agents of the present invention can also be interconverted as by esterification, reaction with ethyl chloroformate to produce ethoxy-carbonyl derivatives which can then be hydrolyzed to hydroxy derivatives. Amine oxides are also readily formed by oxidation of the amines with peracetic acid in ether solution, and the amine oxides are also effective analgesics and tranquilizing agents.

EXAMPLE 19

4-Ethoxycarbonyl-1-(2-[8-Chloro-5-methoxy-3,4-dihydronaphthyl]methyl)piperazine 1-(2-[8-Chloro-5-methoxy-3,4-dihydronaphthyl]methyl)piperazine (1.0 g., 3.4 mmoles) was slurried with 50 ml. of tetrahydrofuran and ethyl chloroformate (0.432 g., 4.1 mmoles) was added to the slurry dropwise at room temperature. The resulting mixture was stirred for one hour after which another 1.7 mmoles of ethyl chloroformate was added and the final mixture stirred overnight. The product which precipitated from the mixture was collected on a filter, washed with tetrahydrofuran and dried, m.p. 195° C. The yield was 550 mg. An additional 197 mg., m.p. 185°–195° C., was recovered from the mother-liquor.

EXAMPLE 20

Propionate Ester of 1-(2-[8-Chloro-5-methoxy-3,4-dihydronaphthyl]methyl)-4-hydroxypiperidine A flask was charged with 25 ml. methylene chloride, 1.0 g. (3.2 mmoles) of 1-(2-[8-chloro-5-methoxy-3,4-dihydronaphthyl]methyl)-4-hydroxypiperidine and 1.0 g. of pyridine. The solution was cooled in an ice-bath and 325 mg. (3.5 mmoles) of propionyl chloride in 10 ml. $CH_2Cl_2$ was added dropwise. The ice-bath was then removed and the mixture stirred at room temperature for 3 hours. After then washing the mixture with dilute aqueous acid, dilute base, water and finally with brine, the extracts were dried over solid $Na_2SO_4$ and evaporated to dryness to afford a brown oil which crystallized upon standing, 768 mg. Purification by silica gel chromatography, eluting with ethanol-benzene (2:1) and precipitation with anhydrous hydrogen chloride from ether solution gave 584 mg. of the hydrochloride salt of the title compound, m.p. 230°–235° C. (49% yield).

Anal. Calc'd for $C_{20}H_{26}O_3NCl \cdot HCl$ (percent):C, 60.00; H, 6.75; N, 3.50 Found (percent):C, 59.46; H, 6.85; N, 3.34

EXAMPLE 21

1-(2-[8-Chloro-5-methoxy-3,4-dihydronaphthyl]methyl)-4-acetoxy-4-phenylpiperidine and the corresponding Acetoacetate A mixture of 1-(2-[8-chloro-5-methoxy-3,4-dihydronaphthyl]methyl-4-hydroxy-4-phenylpiperidine hydrochloride (1.30 g., 3.1 moles), acetyl chloride, (256 mg., 3.3 mmoles), triethylamine (650 mg., 6.5 mmoles) and methylene chloride, 100 ml., was stirred at room temperature for 60 hours. The reaction mixture was then made alkaline and washed with water, the organic layer dried over $MgSO_4$ and evaporated to dryness. The residue was chromatographed on a silica gel column, eluting with 4:1 benzene-ethyl acetate and collecting 50 ml. fractions. After 30 fractions had been collected, fractions 4–13 were combined and rechromotographed eluting with 9:1 benzene-ethyl acetate taking fractions in the same manner. Rechromatography fractions 5 and 6 were combined and converted to the hydrochloride salt to obtain 70 mg. of the acetoxy compound, m.p. 118°–121° C. Identified by mass spectrum, M+ 426.

Rechromatography fractions 9 and 10 were worked up in a similar manner to afford 43 mg. of the corresponding acetoacetate, m.p. 123°–124° C. which was also identified by mass spectrum, M+ 467.

EXAMPLE 22

6-Isopropoxy-1-tetralone

Commercial 6-methoxy-1-tetralone (50 g., 0.284 mole) was dissolved in 200 ml. glacial acetic acid and 300 ml. of 48% hydrobromic acid was added. The resulting solution was refluxed for 24 hours, then allowed to stir and cool to room temperature overnight. The reaction mixture was poured into 1 liter of cool water, the resulting slurry extracted with 500 ml. ethyl acetate and the aqueous layer extracted again with 2 × 200 ml. ethyl acetate. The combined organic layers were washed with 2 × 200 ml. water then carefully washed with saturated $NaHCO_2$ solution (foaming) until acidic products are neutralized. The organic extracts were dried over saturated aqueous NaCl solution then with solid $MgSO_4$ and carbon treated. After filtration, the extracts were evaporated to dryness to afford 38.1 g. of 6-hydroxyl-1-tetralone, m.p. 151°–152.5° C. (83% yield).

In 100 ml. of dry acetone, ten grams (0.062 mole) of the above product was combined with equimolar amounts of isopropyl iodide (7 ml.) and $K_2CO_3$ (8.56 g.). Under a nitrogen atmosphere the mixture was stirred at reflux overnight whereupon an additional 7 ml. of isopropyl iodide was added. After again refluxing for an additional 2 hours, the final reaction mixture was cooled, insoluble material removed by filtration, and the filtrate evaporated to dryness. The unvaporized residue was dissolved in ether and washed with three ml. portions of 10% aqueous NaOH to remove unreacted starting material. The washed ether solution was then dried over brine, followed by solid $MgSO_4$ and evaporated to dryness to obtain the title compound as an amber liquid, 12.7 g., 87% yield.

Obviously many modifications and variations of the present invention are possible in the light of the above teachings. It is, therefore, to be understood that within the scope of the appended claims the invention may be practiced otherwise than as specifically described.

What is claimed is:

1. A compound having the formula

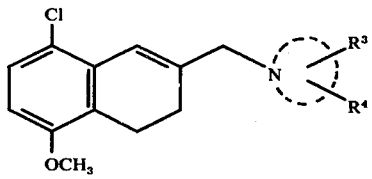

wherein the nitrogen containing ring is selected from the group consisting of morpholino, thiazolidino, pyrrolidino, piperidino, piperazino and 3,4-[dihydropiperidino] dehydropiperidino;

$R^3$, when taken separately, is a member selected from the group consisting of hydrogen, hydrocarbyl having up to six carbon atoms and free of triple bonds, pyrrolidino, piperidino, phenyl and phenyl substituted by Cl, Br or $CF_3$;

$R^4$, when taken separately, is a member selected from the group consisting of hydrogen, hydroxyl, alkoxy having up to four carbon atoms, alkanoyloxy having up to six carbon atoms, acetoacetoxy, alkylcarbonyl having up to four carbon atoms, carboxamido, N-alkylcarboxamido having up to seven carbon atoms and the moiety

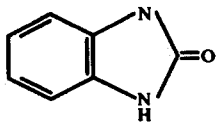

with the proviso that when R⁴ is said moiety, said nitrogen containing ring is piperidino or 3,4-dehydropiperidino and R³ and R⁴, when taken together, are

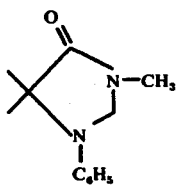

with the proviso that said nitrogen containing ring is piperidino.

2. A compound of claim 1 wherein the ring containing the nitrogen atom is piperidino, R³ is 4-p-chlorophenyl and R⁴ is 4-hydroxy.

3. A compound of claim 1 wherein the ring containing the nitrogen atom is piperidino, R³ is 4-phenyl and R⁴ is 4-ethoxy.

4. A compound of claim 1 wherein the ring containing the nitrogen atom is piperidino and R³ and R⁴ taken together are

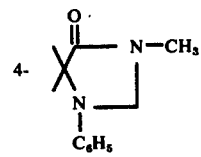

5. A compound of claim 1 wherein the ring containing the nitrogen atom is piperidino, R³ is 4-phenyl and R⁴ is 4-acetoxy.

6. A compound of claim 1 wherein the ring containing the nitrogen atom is pyrrolidino, R³ is hydrogen and R⁴ is hydrogen.

7. A compound having the formula

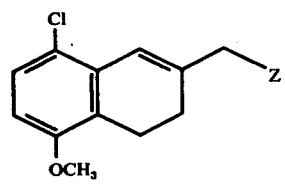

in which Z is a member of a group consisting of pyrrolidino, 3-hydroxy-3-phenylpyrrolidino, 4-carboxamidopiperidino, 4-acetoxy-4-phenylpiperidino, 4-ethoxy-4-phenylpiperidino, 4-hydroxy-4-(4-chlorophenyl)-piperidino, 4-methylpiperazino, 4-(2-hydroxyethyl)-piperazino and

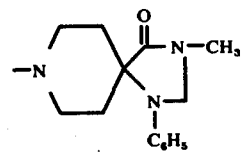

8. 1-(2-[8-chloro-5-methoxy-3,4-dihydronaphthyl]-methyl)-4-acetoxy-4-phenylpiperidine.

9. 1-(2-[8-chloro-5-methoxy-3,4-dihydronaphthyl]-methyl)pyrrolidine.

* * * * *